(12) United States Patent
Naima

(10) Patent No.: US 10,004,408 B2
(45) Date of Patent: Jun. 26, 2018

(54) METHODS AND SYSTEMS FOR DETECTING PHYSIOLOGY FOR MONITORING CARDIAC HEALTH

(71) Applicant: ReThink Medical, Inc., San Francisco, CA (US)

(72) Inventor: Reza Naima, San Francisco, CA (US)

(73) Assignee: ReThink Medical, Inc., San Francisco, CA (US)

( * ) Notice: Subject to any disclaimer, the term of this patent is extended or adjusted under 35 U.S.C. 154(b) by 0 days. days.

(21) Appl. No.: 14/958,915

(22) Filed: Dec. 3, 2015

(65) Prior Publication Data

US 2016/0183813 A1 Jun. 30, 2016

Related U.S. Application Data

(60) Provisional application No. 62/086,910, filed on Dec. 3, 2014.

(51) Int. Cl.
*A61B 5/0205* (2006.01)
*A61B 5/0245* (2006.01)
(Continued)

(52) U.S. Cl.
CPC ...... *A61B 5/02055* (2013.01); *A61B 5/02416* (2013.01); *A61B 5/0537* (2013.01);
(Continued)

(58) Field of Classification Search
None
See application file for complete search history.

(56) References Cited

U.S. PATENT DOCUMENTS 5,971,930 A 10/1999 Elghazzawi
6,496,725 B2 12/2002 Kameda et al.
(Continued)

FOREIGN PATENT DOCUMENTS

CA 2333062 A1 12/1999
CA 2375249 A1 12/2000
(Continued)

OTHER PUBLICATIONS

Adamson et al.; "Continuous autonomic assessment in patients with symptomatic heart failure: prognostic value of heart rate variability measured by an implanted cardiac resynchronization device"; Circulation; 110(16); pp. 2389-2394; Oct. 19, 2004.
(Continued)

*Primary Examiner* — Brian T Gedeon
(74) *Attorney, Agent, or Firm* — Shay Glenn LLP

(57) ABSTRACT

In one aspect, a photoplethysmograph system to measure a user's heart rate includes one or more light-emitting diodes (LED) that provide a constantly-on light signal during a measurement period. The one or more light-emitting diodes are in optical contact with an epidermal surface of the user. The one or more light-emitting diodes emit a light signal into the tissue of the user, and wherein the tissue contains a pulsating blood flow. A light-intensity sensor circuit converts the reflected LED light from the tissue into a second signal that is proportional to a reflected light intensity. The second signal includes a voltage or current signal. A computer-processing module calculates the user's beat-to-beat heart rate from the second current signal.

14 Claims, 10 Drawing Sheets

(51) Int. Cl.
*A61B 5/00* (2006.01)
*A61B 5/024* (2006.01)
*A61B 5/053* (2006.01)
*A61B 5/11* (2006.01)

(52) U.S. Cl.
CPC .......... *A61B 5/7225* (2013.01); *A61B 5/0002* (2013.01); *A61B 5/0535* (2013.01); *A61B 5/1118* (2013.01); *A61B 5/6831* (2013.01); *A61B 5/7207* (2013.01); *A61B 2562/046* (2013.01)

(56) References Cited

U.S. PATENT DOCUMENTS

| | | |
|---|---|---|
| 6,516,222 B2 | 2/2003 | Fukuda |
| 6,714,813 B2 | 3/2004 | Ishigooka et al. |
| 6,821,249 B2 | 11/2004 | Casscells et al. |
| 6,829,496 B2 | 12/2004 | Nagai et al. |
| 6,850,788 B2 | 2/2005 | Al-Ali |
| 6,896,661 B2 | 5/2005 | Dekker |
| 7,018,339 B2 | 3/2006 | Birnbaum et al. |
| 7,024,233 B2 | 4/2006 | Al-Ali et al. |
| 7,215,987 B1 | 5/2007 | Sterling et al. |
| 7,547,279 B2 | 6/2009 | Kim et al. |
| 7,657,295 B2 | 2/2010 | Coakley et al. |
| 7,740,591 B1 | 6/2010 | Starr et al. |
| 7,761,261 B2 | 7/2010 | Shmueli et al. |
| 7,794,406 B2 | 9/2010 | Reisfeld et al. |
| 7,976,472 B2 | 7/2011 | Kiani |
| 8,092,393 B1 | 1/2012 | Rulkov et al. |
| 8,148,686 B2 | 4/2012 | Ryhänen et al. |
| 8,175,671 B2 | 5/2012 | Hoarau |
| 8,233,974 B2 | 7/2012 | Ward et al. |
| 8,328,718 B2 | 12/2012 | Tran |
| 8,346,328 B2 | 1/2013 | Mannheimer et al. |
| 8,374,688 B2 | 2/2013 | Libbus et al. |
| 8,401,608 B2 | 3/2013 | Baker et al. |
| 8,412,317 B2* | 4/2013 | Mazar ............... A61B 5/0531 600/547 |
| 8,433,383 B2 | 4/2013 | O'Neil et al. |
| 8,600,468 B2 | 12/2013 | Yamamoto et al. |
| 8,721,555 B2 | 5/2014 | Westbrook et al. |
| 8,744,577 B2 | 6/2014 | Joo et al. |
| 8,836,345 B2 | 9/2014 | Chetham et al. |
| 8,886,271 B2 | 11/2014 | Kiani et al. |
| 8,903,484 B2 | 12/2014 | Mazar |
| 8,920,332 B2 | 12/2014 | Hong et al. |
| 8,945,017 B2 | 2/2015 | Venkatraman et al. |
| 8,954,135 B2 | 2/2015 | Yuen et al. |
| 8,956,303 B2 | 2/2015 | Hong et al. |
| 8,965,471 B2 | 2/2015 | Lamego |
| 8,974,396 B1 | 3/2015 | Brady et al. |
| 8,977,348 B2 | 3/2015 | Su et al. |
| 8,998,815 B2 | 4/2015 | Venkatraman et al. |
| 9,044,149 B2 | 6/2015 | Richards et al. |
| 9,044,171 B2 | 6/2015 | Venkatraman et al. |
| 9,049,998 B2 | 6/2015 | Brumback et al. |
| 9,113,794 B2 | 8/2015 | Hong et al. |
| 9,130,070 B2 | 9/2015 | Deliwala et al. |
| 9,149,235 B2 | 10/2015 | Ward et al. |
| 9,186,108 B2 | 11/2015 | Rodriguez-Llorente et al. |
| 9,192,310 B2 | 11/2015 | Rodriguez-Llorente et al. |
| 9,241,635 B2 | 1/2016 | Yuen et al. |
| 9,241,646 B2 | 1/2016 | Addison et al. |
| 9,247,884 B2 | 2/2016 | Yuen et al. |
| 9,289,167 B2 | 3/2016 | Diab et al. |
| 9,304,202 B2 | 4/2016 | Deliwala |
| 9,320,443 B2 | 4/2016 | Libbus et al. |
| 9,339,236 B2 | 5/2016 | Frix et al. |
| 9,504,406 B2 | 11/2016 | Chetham et al. |
| 2008/0214903 A1 | 9/2008 | Orbach |
| 2010/0217096 A1 | 8/2010 | Nanikashvili |
| 2012/0179006 A1 | 7/2012 | Jansen et al. |
| 2012/0253141 A1 | 10/2012 | Addison et al. |
| 2012/0283535 A1 | 11/2012 | Sarussi |
| 2013/0058358 A1 | 3/2013 | Fulton et al. |
| 2013/0072145 A1 | 3/2013 | Dantu et al. |
| 2013/0261415 A1 | 10/2013 | Ashe et al. |
| 2013/0281800 A1 | 10/2013 | Saroka et al. |
| 2014/0018779 A1 | 1/2014 | Worrell et al. |
| 2014/0031713 A1 | 1/2014 | Gaw et al. |
| 2014/0073952 A1 | 3/2014 | Rodriguez-Llorente et al. |
| 2014/0073957 A1 | 3/2014 | Rodriguez-Llorente et al. |
| 2014/0073964 A1 | 3/2014 | Rodriguez-Llorente et al. |
| 2014/0155759 A1 | 6/2014 | Kaestle et al. |
| 2014/0213858 A1 | 7/2014 | Presura et al. |
| 2014/0213863 A1 | 7/2014 | Loseu et al. |
| 2014/0253709 A1 | 9/2014 | Bresch et al. |
| 2014/0276166 A1 | 9/2014 | Drori et al. |
| 2014/0288436 A1 | 9/2014 | Venkatraman et al. |
| 2014/0309537 A1 | 10/2014 | Niwa et al. |
| 2014/0330132 A1 | 11/2014 | Raskin |
| 2014/0343371 A1 | 11/2014 | Sowers et al. |
| 2015/0038810 A1 | 2/2015 | Melker |
| 2015/0065819 A1 | 3/2015 | Thakur et al. |
| 2015/0088002 A1 | 3/2015 | Podhajsky et al. |
| 2015/0088003 A1 | 3/2015 | Podhajsky et al. |
| 2015/0157219 A1* | 6/2015 | Lee ............... A61B 5/02055 600/393 |
| 2015/0164404 A1 | 6/2015 | Euliano et al. |
| 2015/0196256 A1 | 7/2015 | Venkatraman et al. |
| 2015/0223760 A1 | 8/2015 | Greifer |
| 2015/0272488 A1 | 10/2015 | Ueda et al. |
| 2015/0335293 A1 | 11/2015 | Christman et al. |
| 2015/0366469 A1 | 12/2015 | Harris et al. |
| 2016/0015275 A1 | 1/2016 | Samadani et al. |
| 2016/0022157 A1 | 1/2016 | Melker et al. |
| 2016/0022201 A1 | 1/2016 | Arnold et al. |
| 2016/0022220 A1 | 1/2016 | Lee et al. |
| 2016/0029898 A1 | 2/2016 | LeBoeuf et al. |
| 2016/0029953 A1* | 2/2016 | Bonomi ............... A61B 5/0537 600/529 |
| 2016/0058300 A1 | 3/2016 | Yoon et al. |
| 2016/0058375 A1 | 3/2016 | Rothkopf |
| 2016/0089053 A1 | 3/2016 | Lee et al. |
| 2016/0113526 A1 | 4/2016 | Nageshwar et al. |
| 2016/0128586 A1 | 5/2016 | Parton et al. |
| 2016/0128604 A1 | 5/2016 | Eom et al. |
| 2016/0128637 A1 | 5/2016 | LeBoeuf et al. |
| 2016/0206220 A9 | 7/2016 | Robinson |

FOREIGN PATENT DOCUMENTS

| | | |
|---|---|---|
| CA | 2539547 A1 | 3/2005 |
| CA | 2578106 A1 | 12/2005 |
| CN | 101730503 A | 6/2010 |
| CN | 103815888 B | 1/2016 |
| EP | 0985429 B1 | 12/2004 |
| EP | 2219513 B1 | 5/2012 |
| EP | 2687154 A1 | 1/2014 |
| EP | 1948017 B1 | 4/2014 |
| EP | 2896359 A1 | 7/2015 |
| EP | 2155058 B1 | 9/2015 |
| EP | 2443993 B1 | 3/2016 |
| EP | 1898784 B1 | 5/2016 |
| GB | 2316171 B | 11/2000 |
| GB | 2393786 A | 4/2004 |
| GB | 2425180 B | 3/2009 |
| GB | 2520487 A | 5/2015 |
| GB | 2523880 A | 9/2015 |
| JP | 2002159473 A | 6/2002 |
| JP | 2006271949 A | 10/2006 |
| JP | 3856477 B2 | 12/2006 |
| JP | 2013132326 A | 7/2013 |
| JP | 5587774 B2 | 9/2014 |
| JP | 5687994 B2 | 1/2015 |
| JP | 5802748 B2 | 11/2015 |
| JP | 5893922 B2 | 3/2016 |
| KR | 20110136113 A | 12/2011 |
| SG | 189433 A1 | 8/2013 |
| WO | WO2008/067122 A1 | 6/2008 |
| WO | WO2009/064979 A2 | 5/2009 |
| WO | WO2010/117545 A1 | 10/2010 |
| WO | WO2013/019494 A2 | 2/2013 |

(56) References Cited

FOREIGN PATENT DOCUMENTS

| | | |
|---|---|---|
| WO | WO2013/166341 A1 | 11/2013 |
| WO | WO2014/125402 A1 | 8/2014 |
| WO | WO2014/201183 A1 | 12/2014 |
| WO | WO2014/207671 A2 | 12/2014 |
| WO | WO2015/036289 A1 | 3/2015 |
| WO | WO2015/084376 A1 | 6/2015 |
| WO | WO2015/087164 A1 | 6/2015 |
| WO | WO2015/102589 A1 | 7/2015 |
| WO | WO2015/102591 A1 | 7/2015 |
| WO | WO2015/116163 A1 | 8/2015 |
| WO | WO2015/116891 A1 | 8/2015 |
| WO | WO2015/130413 A1 | 9/2015 |
| WO | WO2015/131065 A1 | 9/2015 |
| WO | WO2015/150199 A1 | 10/2015 |
| WO | WO2015/150434 A1 | 10/2015 |
| WO | WO2016/000986 A1 | 1/2016 |
| WO | WO2016/037991 A1 | 3/2016 |
| WO | WO2016/040264 A1 | 3/2016 |
| WO | WO2016/069082 A1 | 5/2016 |
| WO | WO2016/100145 A1 | 6/2016 |

OTHER PUBLICATIONS

Anand et al; "Design and performance of a multisensor heart failure monitoring algorithm: results from the multisensor monitoring in congestive heart failure (MUSIC) study"; J. Card Fail; 18(4); pp. 289-295; Apr. 2012.

Cowie et al; "Development and validation of an integrated diagnostic algorithm derived from parametersmonitored in implantable devices for identifying patients at risk for heart failure hospitalization in an ambulatory setting"; Eur Heart J.; 34(31); pp. 2472-2480; Aug. 2013.

Goetze et al; "Ambulatory respiratory rate trends identify patients at higher risk of worsening heart failure in implantable cardioverter defibrillator and biventricular device recipients: a novel ambulatory parameter to optimize heart failure management"; J Interv Card Electrophysiol.; 43(1); pp. 21-29; Jun. 2015.

Joseph et al; "Acute Decompensated Heart Failure;" Tex Heart Inst J.; 36(6); pp. 510-520; (year of pub. sufficiently earlier than effective US filing date and any foreign priority date) 2009.

Maurer et al; "Rationale and Design of the Left Atrial Pressure Monitoring to Optimize Heart Failure TherapyStudy (LAPTOP-HF)"; J. Card Fail; 21(6); pp. 479-488; Jun. 2015.

Whellan et al; "Combined Heart Failure Device Diagnostics Identify Patients at Higher Risk of Subsequent Heart Failure Hospitalizations"; J. Am. Coil. Cardiol.; 55(17); pp. 1803-1810; Apr. 27, 2010.

Bouchaala et al.; Portable bioimpedance spectrometer for total frequency range of beta-dispersion; tm-Technisches Messen tm-Technisches; 80(11); pp. 373-378; Nov. 1, 2013.

Yang et al.; Design and preliminary evaluation of a portable device for the measurement of bioimpedance spectroscopy; Physiol. Meas.; 27(12); pp. 1293-1310; Dec. 2006.

Naima; U.S. Appl. No. 15/791,346 entitled "Methods and systems for physiologic monitoring," filed Oct. 23, 2017.

* cited by examiner

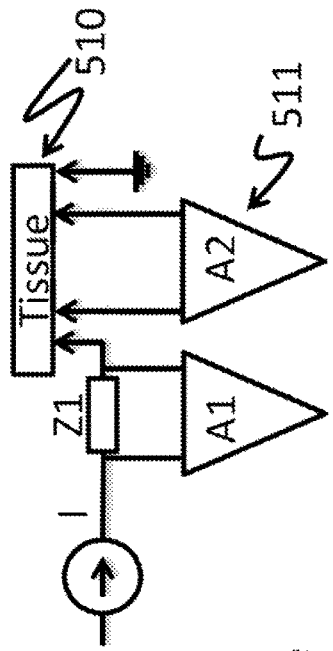
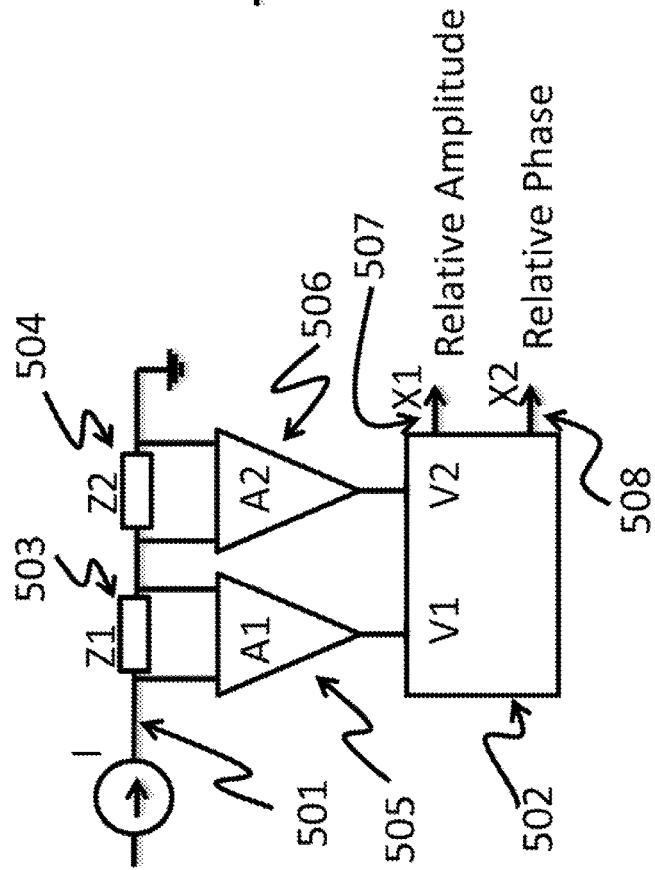
Figure 5B
Figure 5A

METHODS AND SYSTEMS FOR DETECTING PHYSIOLOGY FOR MONITORING CARDIAC HEALTH

CROSS-REFERENCE TO RELATED APPLICATIONS

This application hereby incorporates by reference the following applications in their entirety: U.S. Provisional Patent Application No. 62/086,910, titled METHODS AND SYSTEMS FOR DETECTING PHYSIOLOGY FOR MONITORING CARDIAC HEALTH and filed on 3 Dec. 2014.

FIELD

This application relates generally medical devices, and more particularly to a system, apparatus and method of measuring a number of physiologic parameters which can be used for quantification of heart failure status.

BACKGROUND

Overall, 5.8 million individuals in the United States suffer from heart failure (HF) and one in ten elderly develops HF. Despite advances in treatment and relative improvement in survival, the rate of HF hospitalizations has surpassed one million yearly with HF becoming the leading hospital diagnosis for Medicare patients. The costs for HF care are close to $40 billion annually and this represents a large cost to the Medicare system. More than two-thirds of the costs are related to HF hospitalizations, as a result of suboptimal disease management, with roughly 25% of patients readmitted within 30-days of hospital discharge.

A major barrier in preventing HF related hospitalization is the current reactive standard of care, which involves relying on a patient self-reported daily weight to determine if a sudden increase in body fluid weight has occurred. Unfortunately, body weight has been shown to be an unreliable marker for cardiac decompensation, and suffers from very low patient compliance. It is worth emphasizing that the population of individuals who suffer from heart failure are predominantly elderly and thus have a very hard time following instructions, often forgetting their tasks or are unmotivated to follow instructions.

At least fifty percent (50%) of HF related hospitalizations are preventable, and that early detection of symptoms can led to a fifty-six percent (56%) reduction in mortality in this population, simple and reliable non-invasive methods to detect early HF decompensation are missing. New tools for HF outpatient monitoring and management can reduce its high morbidity.

Several studies conducted in HF patients that have cardiac implantable electronic devices (CIED) capable of monitoring physiologic parameters have shown that trending these parameters can predict a HF decompensation before it occurs. Unfortunately, such devices are used in less than a third of HF patients, require a surgical procedure to implant the device and need in home remote setup, adding to the complexity of the disease management process.

BRIEF SUMMARY OF THE INVENTION

In one aspect, a bioimpedance spectrometer system includes two current-delivery electrodes that convey an alternating current (AC) signal through a user's tissue, wherein the two current-delivery electrodes are placed in contact with a surface of the user's tissue. The bioimpedance spectrometer system includes two sense electrodes that measure the differential voltage on the tissue. An instrumentation amplifier measures the differential voltage on the surface of the user's tissue through the two sense electrodes, and generates a voltage measurement signal corresponding to the difference in voltage between each of the two sense electrodes. A low-impedance or high-impedance current source circuit maintains a specified-range value of the alternating current (AC) current passing through the user's tissue such that the magnitude of a tissue impedance is equal to a differential voltage between two sense electrodes on the tissue divided by a known or measured current provided by the current source circuit. A processing module calculates an impedance magnitude or a complex impedance value calculated from the impedance magnitude and a phase shift between the differential voltage and the AC current and determines a relative amount of intracellular and extracellular fluid from the impedance magnitude or complex impedance value.

In another aspect, a photoplethysmograph system to measure a user's heart rate includes one or more light-emitting diodes (LED) that provide a constantly-on light signal during a measurement period. The one or more light-emitting diodes are in optical contact with an epidermal surface of the user. The one or more light-emitting diodes emit a light signal into the tissue of the user, and wherein the tissue contains a pulsating blood flow. A light-intensity sensor circuit converts the reflected LED light from the tissue into a second signal that is proportional to a reflected light intensity. The second signal includes a voltage signal or a current signal. A computer-processing module calculates the user's beat-to-beat heart rate from the second current signal.

In yet another aspect, a computerized system for measuring one or more physiologic parameters used to quantify a cardiac state related to heart failure includes a heart rate sensor means that measures the physiologic parameters used to quantify the cardiac state related to a heart failure state. A telemetry system means that communicates the physiologic parameters to a data analysis means. A data analysis means that receives the physiologic parameters and determines a cardiac state.

BRIEF DESCRIPTION OF THE DRAWINGS

FIGS. 5 A-C illustrates example implementations of aspects of a bioimpedance spectrometer, according to some embodiments.

Figure 1:
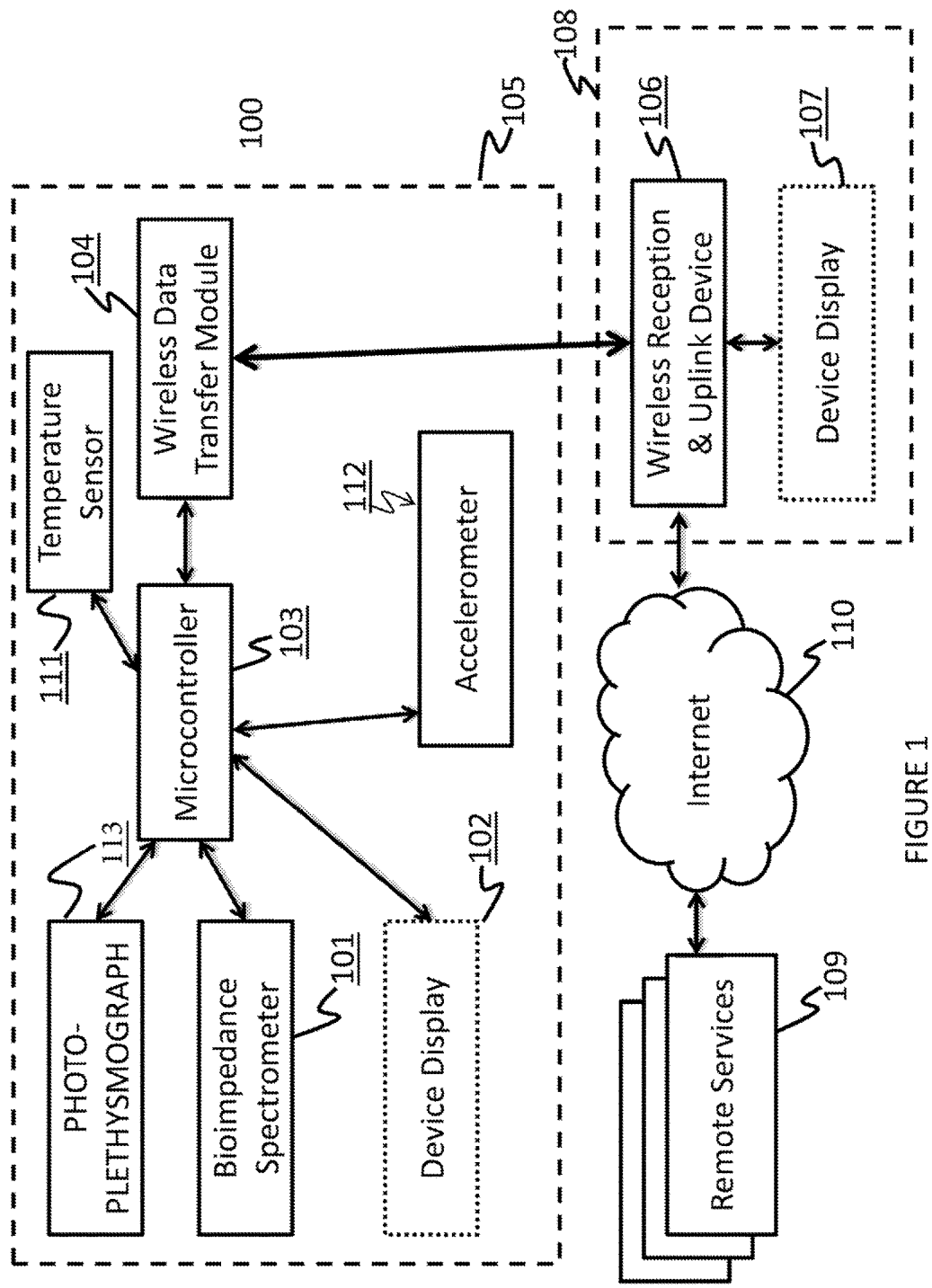
FIG. 1 illustrates an example system for implementing various embodiments.

The Figures described above are a representative set, and are not an exhaustive with respect to embodying the invention.

DESCRIPTION

Disclosed are a system, method, and article of manufacture for measuring a number of physiologic parameters that can be used for quantification of heart failure status. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Bioimpedance can be a measure of the impedance of tissue.

Photoplethysmograph can be a device used to optically obtain a volumetric measurement of an organ. For example, the volume of a blood vessel.

Exemplary Systems, Use Cases and Computer Architecture

FIG. 1 illustrates an example system 100 for implementing various embodiments. System 100 can be a user-wearable computing system. System 100 can include various sensor systems that obtain various physiologic metrics. Said physiologic metrics can be used to predict cardiac decompensation (e.g. worsening heart failure state). Example physiologic metrics include, inter alia: heart rate (HR), heart rate variability (HRV); activity levels; respiration rate (RR); pitting edema (e.g. peripheral edema); etc. Some metrics can be measured directly, such as heart rate, which are then used to derive other metrics, such as heart rate variability.

In one example, system 100 can be a non-invasive system for ambulatory monitoring of heart failure (HF) patients. System 100 can be utilized to predict a HF exacerbation before it manifests in a hospitalization event (e.g. several days, several hours, etc.). System 100 can include systems to alert patients, caregivers and healthcare providers, and/or enable proactive treatment while patients remain at home or another environment. System 100 can include various hardware sensors (and their concomitant driver systems) to, inter alia, monitor relevant physiologic metrics (e.g. see infra) such as peripheral edema. In one example, system 100 can be worn on different parts of the body (e.g. wrist, other areas of the arms, ankles, head mounted, chest, etc.). System 100 that has either capacitive or galvanic contact with the epidermis of the user (e.g. ECG electrodes) as well as optical contact (e.g. finger blood-oxygen saturation monitor). Example locations can be convenient and comfortable for the user when worn but also have access to measure vascularization and/or various areas where edema can occur. System 100 can also incorporate various wireless technology standards for exchanging data of over short distances (e.g. short-wavelength Ultra high frequency (UHF), Bluetooth®, ANT, ANT+, Wi-Fi, and/or ultrasonic-based telemetry systems, etc.). System 100 can also incorporate a wireless module enabling communications over a cellular network (e.g. GSM module)

System 100 can include a user interface to elicit user information and symptoms. System 100 can include a user interface that provides information and/or feedback to the user. System 100 can include a user interface that provides bidirectional communications. This can be incorporated onto the device itself as a simple user interface (i.e. LED/OLED display with buttons), though a web portal, through a smartphone application, augmented-reality elements in a head-mounted display and/or through a stand-alone device. System 100 can include the ability to ask specific questions to a user and thus, increase the sensitivity of the system and decrease the rate of false positives. Rather than, or in addition to, a user interface, especially for individuals who suffer from dementia or are otherwise incapable or interacting with hardware, a call center can call the individuals when it is detected that the hardware is not being worn properly or when the measured data demonstrates some level of cardiac decompensation and further data can be collected to ensure a low false-positive (or for any other reason), or to provide instructions to the individual.

System 100 can include one or more temperature sensors 111 to measure skin and/or ambient temperature. The skin temperature sensors can be exposed through the device to make contact to the skin. The skin temperature sensors can be coupled via a highly temperature conductive material to the skin and/or in close proximity to the skin. The skin temperature sensors can be encapsulated in the same material as rest of system 100. Additionally, the ambient-temperature sensor can be exposed through the system 100 to make contact to the air. The ambient-temperature sensor can be coupled via a highly temperature-conductive material to outside surface of the device and/or in close proximity to the outside of the device encapsulated in the same material as rest of system 100. The sensors can consist of a dedicated integrated circuit (e.g. MCP9700), a thermistor, a thermocouple with amplifier, a passive infrared sensor, a thermopile, etc.

System 100 can include one or more processors to implement algorithms to combine the measured data into a clinically-relevant predictor of worsening HF (e.g. a cardiac decompensation event). When a decompensation event is detected, system 100 can notify the user by providing feedback through the device itself (e.g. display and/or LEDs, audio alerts, haptic alerts, etc.), though a smartphone (e.g. via telemetry), through an appliance, through a web portal and/or by a call center contacting the patient and/or the patients care-giver or physician contacting a specified care giver.

System 105 can include the user-wearable aspect of system 100. System 105 can include various miniature electronic devices that are worn by the bearer under, with or on top of clothing (e.g. such as those provided in FIG. 1). Various information obtained by the subsystems of system 105 can be communicated to wireless communication and/or uplink device 106 (e.g. for storage in a data store, further processing, etc.). System 108 can be another computing system such a personal computer, laptop computer, tablet computer, smart phone, head-mounted display computer, etc. System 108 can also include any Wi-Fi access point. System 108 can also include a device display 107 for providing information to a user. Remote services 109 can include additional computerized-services such patient monitoring services, medical-provider servers, insurance servers, medical-study servers, etc. Remote services 109 can use the measured physiologic data to compute the probability of cardiac decompensation. Remote services 109 can communicate with system 105 and/or system 108 via the Internet 110. Various examples of remote services are provided herein. In some embodiments, various portions of system 105 and system 108 can be integrated into a single device and/or be implemented as a virtual computing system(s). In some embodiments, various portions of system 105, system 108 and/or remote services 109 can be implemented in a cloud-computing environment. In one example, 105 and/or 108 can relay data to the cloud via a direct Wi-Fi connection, a wireless data link to a smartphone, an appliance or personal computer application. The smartphone, appliance or personal computer application can provide feedback. The feedback can be generated from various servers implemented in the cloud (e.g. a cloud-computing platform) for display to the end user, or can prompt the user for additional information and/or other type of interface.

Photoplethysmograph 113 can optically obtain a volumetric measurement of an organ, in particular, the blood vasculature in tissue. As the heart beats, pulses of blood are sent through the arteries and into the capillaries. These expand under the pulsatile pressure, reducing the transmission of light propagating through the tissue. Photoplethysmograph 113 can sense the variations in light transmission corresponding to the variation in wave caused by these pulsatile pressure changes. The rate of the arrival of these waves can be interpreted by system 100 as the heart rate. For example, system 100 can measure the number of waves over a period of time (e.g. number of waves over 10 seconds*6=heart rate in beats per minute) and/or by measuring the time between any two fiduciary points (e.g. minima, maxima, zero crossing, maximum slope, minimum slope, or derived from a wavelet transform etc.) and computing the inverse to derive pulse rate. Accordingly, heart rate variability can be determined by various methods. For example, it can be computed as the standard deviation of the interpulse or interbeat interval (time between two successive pulses) over a period of time. The accuracy of the derived measure can be a function of the accuracy by which the interbeat can be measured. Other examples include the standard deviation of 5 minute mean heart rate values over 24 hours, or a frequency analysis of several minutes' worth of interbeat intervals and measuring the ratio of energy in a particular frequency band (e.g. 0.15 to 0.4 Hz) to that in another band (e.g. 0.04 to 0.15 Hz). System 100 can determine an interbeat interval. An example photoplethysmograph design that can be utilized for photoplethysmograph 113 is provided infra.

System 100 can utilize this information to also determine a respiration rate. For example, two methods for determining respiration rate are now provided. System 100 can utilize either one, or a combination of the two. One method relies on the respiratory sinus arrhythmia (RSA) that is the parasympathetically mediated slowing down of the heart rate during exhalation and speeding up during inhalation. A plot of the instantaneous heart rate (e.g. a tachogram) can be correlated to a respiratory rate. The respiration rate is then measured the same way the heart rate is measured from this waveform (e.g. peak to peak interval).

A secondary method can include examining the low frequency component of the photoplethysmograph. Variations in pulmonary pressure (e.g. as a result of respiration) can result in minute blood pressure variations and can be picked up by the photoplethysmograph. By filtering the photoplethysmograph for the frequencies that correspond to respiration, a waveform corresponding to respiration can be detected and used to measure respiratory rate.

Bioimpedance spectrometer 101 can be used to measure the complex impedance and/or opposition to the flow of an electric current through the user's tissue. For example, bioimpedance spectrometry can be used to quantify fluid compartmentalization. For example, bioimpedance spectrometer 101 can quantify/measure peripheral edema (e.g. pitting edema). Worsening peripheral edema can be utilized as a predictor of decompensation in HF patients and is thus a method of characterizing the state of cardiac decompensation. For example, bioimpedance spectrometer 101 can be incorporated into system 100 implemented as a user-wearable device. Example implementations of various bioimpedance spectrometers are provided infra. It is noted that in some examples, in lieu of complex impedance the magnitude of the impedance can be utilized.

Bioimpedance spectrometer 101 can be used to measure heart rate. 101 can be operated at a fixed frequency and the change in the magnitude of the impedance can reflect the volumetric changes associated with blood vessels/capillaries expanding as the pulsatile pressure wave arrives from the heart as a result of the heart beating (bioimpedance plethysmography). Thus, by measuring the impedance changes in the tissue, it is possible to measure hear rate, akin to the method used by the photoplethysmogram 113. It is also possible to combine the output of the photoplethysmogram and the bioimpedance plethysmograph (or other heart rate sensing technologies, etc.) to derive a better estimate of the actual heart rate through a number of methodologies, such as the application of a Kalman filter to the signals.

Device display 102 and/or 107 can be an electronic visual display or LEDs, output device for presentation of information for visual or tactile reception (e.g. a touchscreen, etc.).

Accelerometer 112 can be a device that measures proper acceleration and/or rate of change of velocity. Accelerometer 112 can detect the orientation of system 100. For example, user activity, as well as type of activity, can be quantified with a three-axis accelerometer that is incorporated into the hardware. It is noted that in some example embodiments, a piezo-electric sensor can be used to detect heart rate (e.g. pulse rate).

For example, accelerometer 112 can be a one (1), two (2), or (3) axis accelerometer. Accelerometer 112 can be an integrated accelerometer along with other sensors (e.g. gyroscopes, compasses, etc.) and/or microcontrollers. Accelerometer 112 can interface a microcontroller 103 (or other type of processing unit) using an analog and/or a digital interface (e.g. I²C (Inter-Integrated Circuit), Serial Peripheral Interface Bus, etc.). Accelerometer 112 can be configured to detect certain types of motion without having to measure the output continuously, and the microprocessor is notified when an interrupt is triggered (by changing the output voltage on a shared line). This allows microcontroller 103 to enter a low power mode and detect when motion occurs.

Accelerometer 112 can provide motion detection for activity quantification. Accelerometer data can be converted to activity information. An example low-power implementation can utilize a built-in motion detection mechanism to trigger an interrupt that is detected by the microcontroller and used to increment an internal counter. System 100 can record a number of interrupts over configurable duration of time, such as fifteen (15) minutes. The activity level of the user vs. time can then be equal to the number of interrupts recorded in these 'buckets'. Information obtained by any system/device of system 100 can be stored in a local memory and/or remote data storage system (not shown).

Accelerometer 112 can provide motion detection for artifact mitigation. In order to ensure that minimal motion artifacts interrupt the photoplethysmograph and/or bioimpedance measurements, system 100 can first detect a period when there is minimal motion. This is accomplished by starting a timer on microcontroller 103, and waiting for either a period of time to lapse or motion to be detected by the interrupt. When motion is detected before the requite time, then may be too much activity to perform a measurement. System 100 can then wait for a period of time and attempt to detect a period of low activity again. When an activity is not detected, the measurements can commence. If motion is detected during a measurement, then the measurement can be aborted and the system can wait until another period of inactivity. System 100 can predict times that are more opportune for a measurement by keeping track of periods of activity and inactivity over time and computing probabilities of user activity as a function of time or day and/or day of the week. By selecting times to perform measurements that have a higher probability of inactivity, system 100 can conserve power by only testing for inactivity during these periods.

Accelerometer 112 can be used to detect the vibrations resulting from the pulse, especially at a prominent location like the wrist or neck. Small vibrations that occur at a frequency similar to that of the pulse can be used as measure of pulse rate. This measure can be combined with that from the photoplethysmograph or the impedance plethysmograph to derive a better approximation of pulse rate through various techniques such as the application of a Kalman filter.

Wireless communications can be managed by wireless data transfer module 104. Wireless data transfer module 104 can include any data communication systems (e.g. Wi-Fi systems provided supra, cellular data service, mobile satellite communications, wireless sensor networks, etc.).

In other example embodiments, system 100 can include an ECG sensor(s) (not shown for reasons of brevity). ECG sensor(s) can measure electrical activity of the heart. Utilizing the bioimpedance electrodes and/or additional electrodes on the surface of the device (e.g. on the strap of the device, etc.) a user can make contact with the electrodes in various positions (e.g. touching the electrodes with two different hands, etc.).

Figure 2:
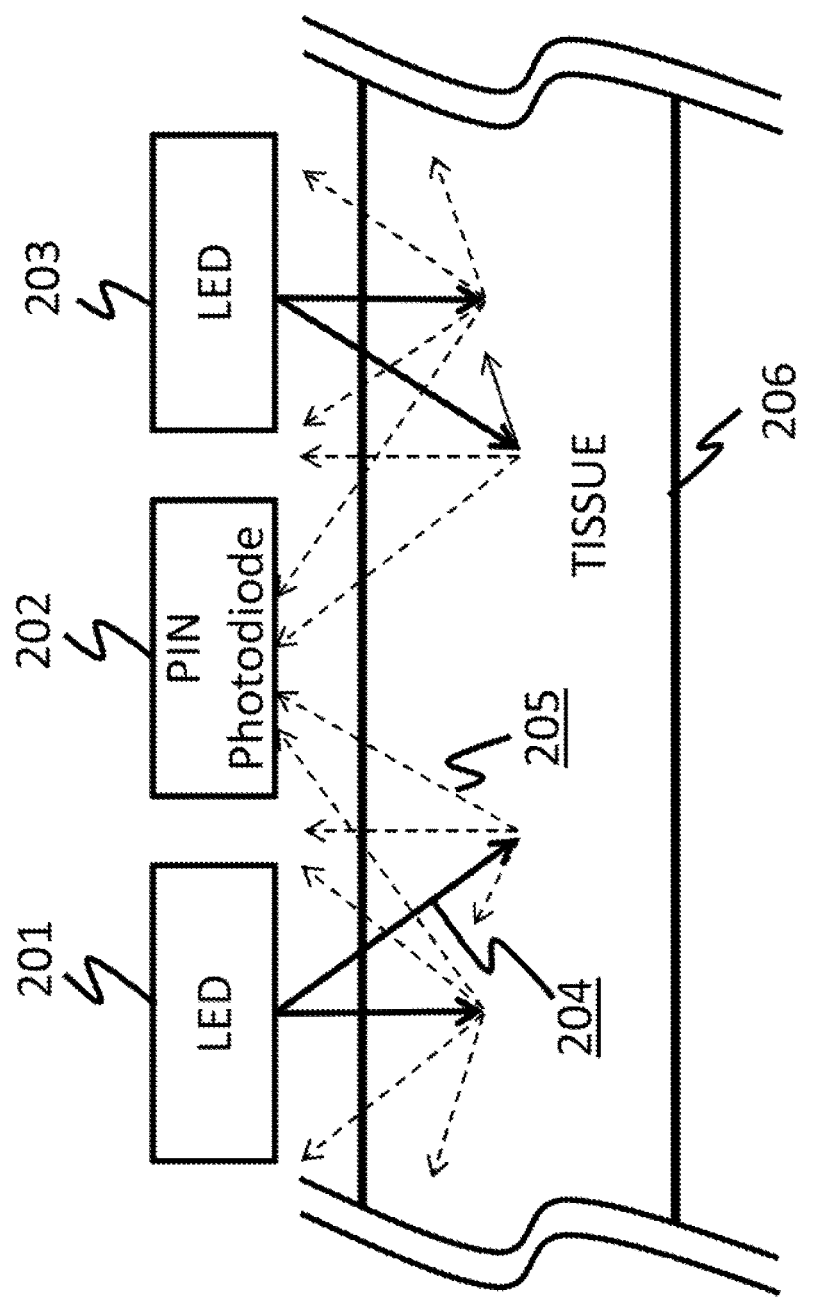
FIG. 2 depicts an example of a photoplethysmograph system used to measure heart rate, according to some embodiments.

FIG. 2 depicts an example of a photoplethysmograph system 200 used to measure heart rate, according to some embodiments. FIG. 2 demonstrates the path that light can take as it travels from the LED to a photodiode, passing through light absorbing tissue which modulate the light intensity as a function of tissue volume (e.g. the varying blood volume). Photoplethysmograph system 200 can include one or more light emitting diodes (LEDs) 201 and/or 203 and one or more PIN photodiode(s) 202 (or other light sensing device, such as a PN photodiode or a phototransistor). PIN photodiode 202 can include a semiconductor device that converts reflected light 205 from emitted LED light 204 into a current or voltage proportional to the light intensity. The current signal can then be measured and interpreted (e.g. as the user's heart rate). As noted supra, as the heartbeats, pulses of blood are sent through the arteries and into the capillaries. These expand under the pulsatile pressure, decreasing the transmission and/or reflection of light propagating through the tissue. Photoplethysmograph system 200 can sense the variations in light transmission corresponding to the variation in the pulse wave caused by these pulsatile volume changes. In one example, the variations in reflected/transmitted light intensity can be measured. Photoplethysmograph system 200 can be placed in contact (e.g. optical contact) with a user's tissue 206 (e.g. on a write, ankle, etc.). In one example, only a single frequency of LED light can be used, originating from one or more LEDs. The LED(s) can be set to provide a constantly-on light source during a measurement period, unlike other implementations that pulse the light on and off. This allows for the signal processing electronics to have a very narrow bandwidth corresponding to the frequency band that is physiologically relevant (e.g. the range of frequencies that correspond to the pulsatile wave) such that the external noise (e.g. external light, motion) can be filtered out, yielding a greater signal to noise ratio.

Figure 3:
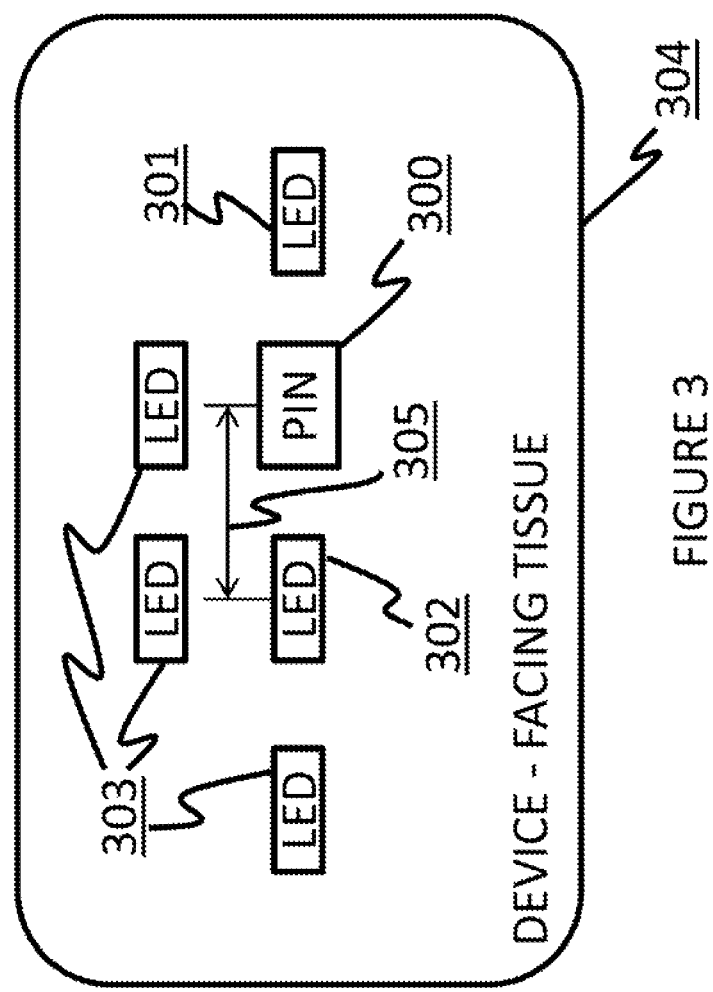
FIG. 3 illustrates an example photoplethysmograph system used to measure heart rate, according to some embodiments.

FIG. 3 illustrates an example photoplethysmograph system 300 used to measure heart rate, according to some embodiments. FIG. 3 demonstrates that any distribution of LEDs in space relative to the photodiode is possible, as long as the light intensity is sufficient to scatter in the tissue and reach the photodiode. Photoplethysmograph system 300 can include arrangement 304 of one or more light emitting diodes (LEDs) 301, 302, 303 and a PIN photodiode 300. As noted in FIG. 3, as the distance between the PIN photodiode 300 and the LED (e.g. distance 305 between LED 302 and PIN photodiode 300) increases, the light travels through a greater amount of tissue and thus is modulated a greater extent by the pulsating blood. However, the increased distance reduces the intensity of light received by the photodiode. In some embodiments, multiple LEDs 301 302 and 303 can be used simultaneously around the photodiode to increase the amount of tissue that is sampled, thus, increasing signal-to-noise ratio (SNR). In some embodiments, higher light intensity from one or more LEDs placed further from the PIN photodiode will increase the SNR.

FIG. 4 A illustrates an example of the mechanism by which bioimpedance spectrometry works. When a current source 400 injects a current through tissue 406 via electrodes 401 and 402, the path the current will take depends on the frequency of current. At low frequencies, the current predominantly travels through the extracellular fluid 404 and is blocked by the lipid bilayer in cell membranes 405, whereas at high frequencies, it travels through the lipid bilayer and through the cells 403, reducing the overall impedance. Accordingly, these cell walls can be modeled as capacitors that block low frequency current, but allow high frequency current to pass through. As the frequency increases, more current can flow across the cell walls and through the intracellular fluid. This increase in effective fluid has an effect of decreasing the impedance of the current. By measuring the impedance at different frequencies, the ratio of fluid outside to inside the cells can be quantified, and can be a measure of edema. For example, the level of edema can be quantified as the ratio of fluid outside the cells to the fluid inside the cells.

FIG. 4 B illustrates an example of bioimpedance spectrometer system, according to some embodiments, which operates with two electrodes. A voltage source 410 generates a voltage (Vo) that passes through electrode 416 into tissue 415, through electrode 414 across resistor 413 and back to the voltage source. The voltage drop across resistor 413 (R) is measured (e.g. by instrumentation amplifier 411) to produce voltage 412 ($V_2$). The impedance of the combination of electrodes 416 and 414, and tissue 415 can be determined the relationship ($V_2$(Vo–$V_2$))/R. This is useful in a number of situations (e.g. if the impedance of the electrodes 416 and 414 is much less than the tissue impedance, or if the impedance of the electrodes is constant and the impedance of the tissue is expected to change) but has the disadvantage of allowing the impedance from the electrode skin interface to affect the measurement. It is noted that in some embodiments, various other amplifier systems (e.g. differential amplifiers, a combination of operational amplifiers, etc.) can be used in lieu instrumentation amplifiers.

Figure 4C:
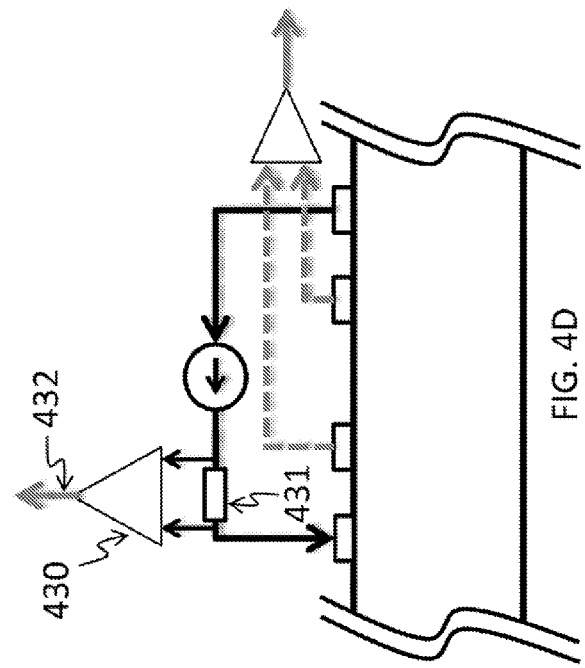
FIG. 4 A-B illustrates and example use of bioimpedance spectrometer system, according to some embodiments.

FIG. 4C illustrates an example use of bioimpedance spectrometer system 101, according to some embodiments, which operates with 4 electrodes and a low impedance current source. Bioimpedance spectrometer system can be placed in contact with a user's tissue as shown through electrodes 421, 425, and a pair of sense electrodes 422 (this is referred to as a tetrapolar configuration). Bioimpedance spectrometer system can generate an alternating current (AC) 420 and convey the current through electrodes 421 and 425 through the tissue. An instrumentation amplifier 411 measures the induced voltage on the skin through pickup electrodes 422 and generates a voltage 424 corresponding to the difference in voltage between the electrodes 422. The amplifier must have a high input impedance to limit the current flow across electrodes 422 that prevents the impedance of electrodes 422 from effecting the measurement. In this configuration, the effects of electrodes 402 and 403 also do not contribute to the measured impedance. The high impedance current source 420 maintains a constant current passing through the tissue and the magnitude of the tissue impedance is equal to the differential voltage 424 divided by the fixed, known, current. The complex impedance can be computed from the impedance magnitude and the phase shift between the measured voltage 406 and the current waveforms 401.

The frequency of the fixed alternating current (AC) can be modified (e.g. from a low frequency (e.g. 1 KHz) to a high frequency (e.g. 1 MHz)) and the measured impedance can be sampled for at various frequencies. By varying the frequency of the AC current 420, the relationship between impedance and frequency can be measured.

Figure 4D:
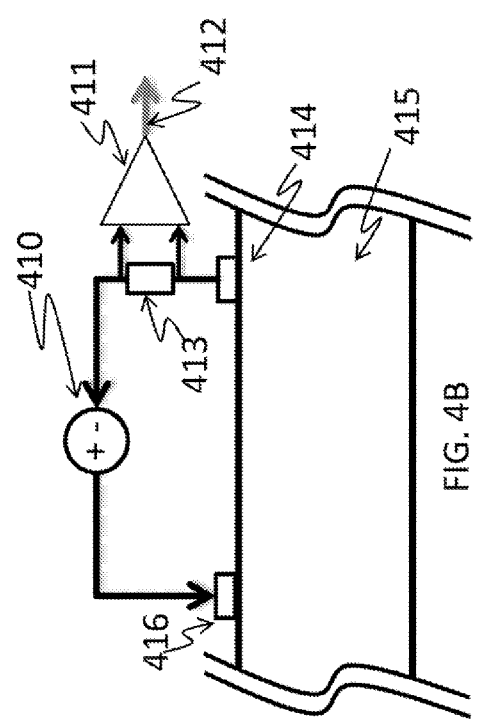
Figure 4A:
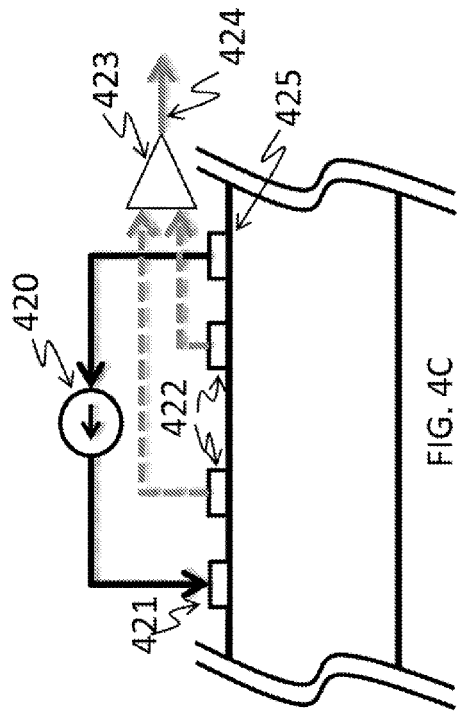
Figure 4B:
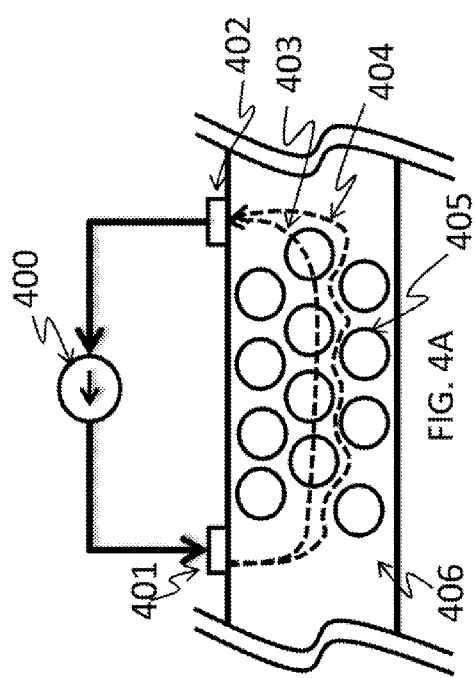

FIG. 4D illustrates an example use of bioimpedance spectrometer system 101, according to some embodiments, which operates with 4 electrodes and a high impedance current source. The operation of this version of the device works the same as in FIG. 4C, however, the tissue and electrode impedance can have an effect on amount of current flowing. To compensate, a measure of the current must be made. FIG. 41 is an example of the addition of a current sense resistor 431 of known fixed value (Rsense), and a mechanism to measure the voltage across the resistor 430 (e.g. instrumentation amplifier) resulting in a voltage 432 (Vsense) to the example in FIG. 4C. In this case, the current is determined by the relationship (Vsense/Rsense). The tissue impedance can thus be computed as the differential voltage across 422 divided by the (Vsense/Rsense).

Bioimpedance spectrometer system 101 can include one or more current sources, voltage sources, and one or more voltage sensors.

By analysis of the measured impedance, (e.g. a fitting impedance to a cole-cole plot and extrapolating the impedance at DC and at infinite frequency, or by comparing the magnitude of the impedance at low and high frequencies), the relative amount of intracellular and extracellular fluid can then be computed.

FIGS. 5 A-B illustrates example implementations of aspects of a bioimpedance spectrometer, according to some embodiments. Bioimpedance spectrometry can be the measure of the impedance (e.g. complex impedance and/or magnitude of impedance) of tissue over a single or range of frequencies. FIG. 5A is an example using a relative gain/phase measurement IC 502 (e.g. Analog Device's AD8302) in measuring the impedance. For a current 501 that flows through two unknown impedances 503 and 504 (e.g. resistors), by measuring the differential voltage across the impedance elements and optionally amplifying the signal through instrumentation amplifiers 505 and 506. The signals can be conditioned (e.g. filtered, scaled, etc.) and applied to the gain/phase measurement IC 502 for measurement of the relative amplitude and phase difference between the signals. The ratio of amplitudes of the input signals can be converted to a voltage that can be measured 507 and quantified by a microcontroller or analog to digital converter. The phase difference between the signals can be converted to a voltage 508 which can be also be measured by a microcontroller or analog to digital converter. If one impedance element is known, value of the other impedance element can be computed. One impedance element 503 or 504 can be replaced by tissue to enable the measurement of the impedance of the tissue. FIG. 5B demonstrates the replacement of 504 by tissue 510. The tissue in either case is connected to four electrodes, as depicted by the arrows in the figure. The system measures the bioimpedance of the tissue between the inner pair of electrodes that are connected to the amplifier, (e.g. 511). The outer two electrodes represent the current source and sink electrodes that may be connected directly to the skin, or AC coupled via one or more capacitors.

More specifically, FIG. 5A depicts a block diagram describing the methodology by which the gain/phase measurement IC 502 can measure an unknown impedance. 'I' 501 represents the current passing through the two impedances. Z1 503 & Z2 504 represent the known and unknown impedances, respectively, A1 505 and A2 506 can represent two instrumentation amplifiers with gains G1 and G2 which output a voltage V1 and V2 that is passed to the relative gain/phase measurement IC (e.g. AD8302). The IC can measure the relative gain and phase, and output it (e.g. the AD8302 has output X1 507, a voltage proportional to the log ratio of input amplitudes (e.g. a log based ten ratio of the V1 over V2) and X2 508, a voltage proportional to the phase difference in the input signals). The unknown impedance Z2 504 can thus computed as $(G1*Z1)/(G2*10^{\wedge}(X1))$.

As stated, in some embodiments, the current source does not need to be low impedance in nature, thus simplifying the design. One embodiment of a current source that does not require low impedance output can be made by a waveform generator (e.g. direct digital synthesis (DDS) IC) that is capable of generating a sine wave with a configurable frequency and or amplitude. The DDS output can be amplified, filtered, and/or scaled (e.g. passive or active filtration, through dedicated ICs or one or more operational amplifiers). The signal can then be fed through a current limiting resistor (Z known), effectively setting the impedance of the current source to the value of the current limiting resistor. The current limiting resistor can be the known impedance resistor 503, or it can be a separate resistor or combination of resistors. Output impedance can range from a few kilo ohms to mega ohms. The resulting current can be calculated as I=V/(Zknown+Ztissue+Zelectrodes) where I is the current; V is the output amplitude of the waveform generator; Zknown is the impedance of the current limiting resistor; Ztissue is the tissue impedance which varies with frequency; and Zelectrodes is the resistance contribution from the electrodes (402 & 403) used to interface the tissue. Thus, one can set the maximum current by selecting V (amplitude), Zknown, and Zelectrodes. The actual current will always be lower due to the addition of Ztissue, so this represents the maximum value. As the tissue impedance varies, the current can vary.

The waveform generator can take on various forms, from a number of passive components forming a tunable oscillator to a voltage-controlled oscillator. A sample implementation can use a direct digital synthesis (DDS) integrated circuit (IC). The DDS IC can use a lookup table and an integrated digital-to-analog converter (DAC) to generate a sine wave. The output of such as signal can be buffered, in some examples, filtered to remove undesired frequency components.

Figure 6:
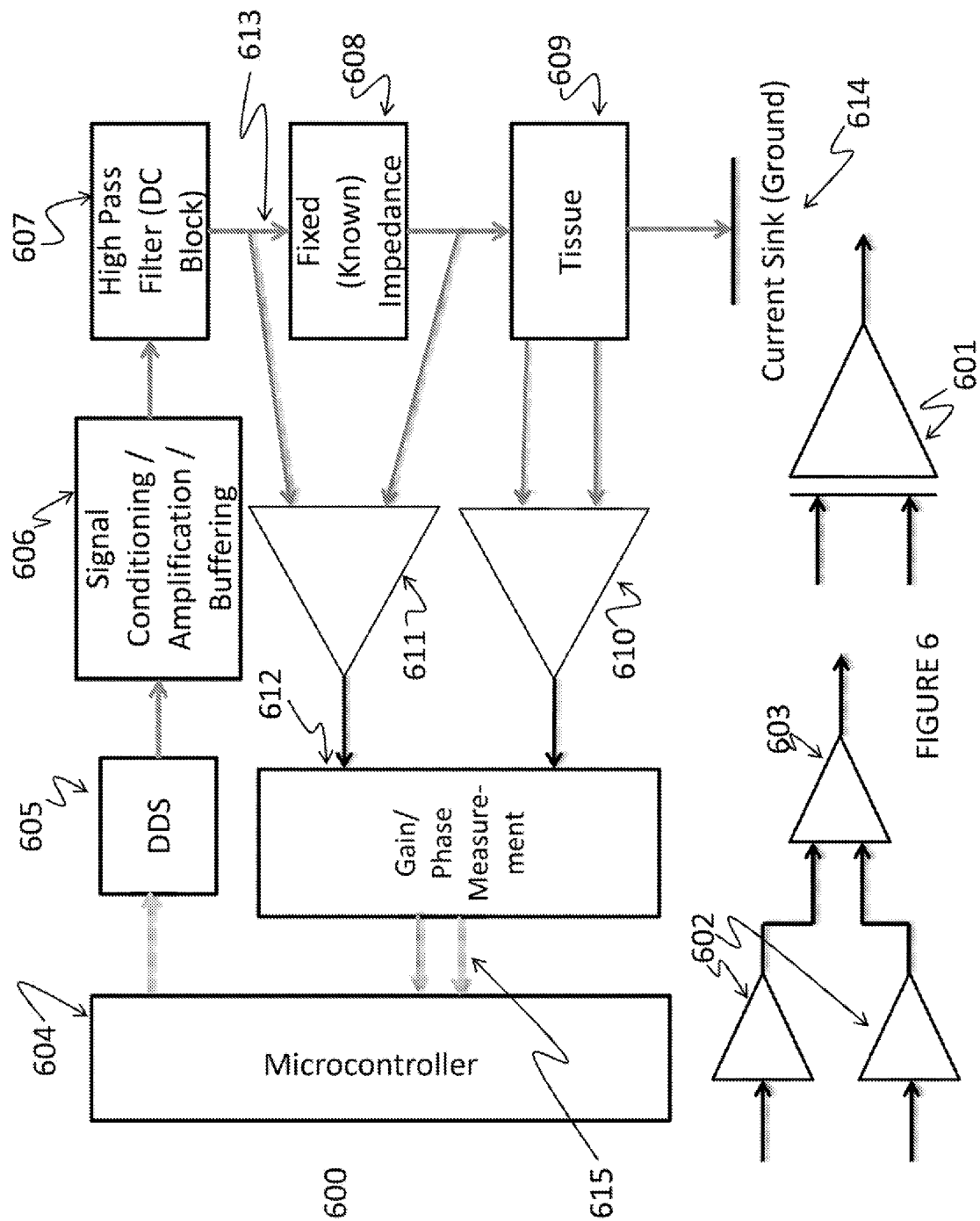
FIG. 6 illustrates a block diagram of example circuits for measuring bioimpedance, according to one example embodiment.

FIG. 6 illustrates circuits 600 for measuring bioimpedance according to one example embodiment. A DDS 605 (e.g. the AD9837) can be controlled by a microcontroller 604 (or FPGA, CPLD, processor, etc.) to output a varying frequency. The signal can then be buffered and filtered 606 to remove any undesired frequency components (e.g. DDS switching noise above 3 MHz). By removing the high frequency components, the waveform can be smoothed out such that it closer resembles a sine wave. This waveform can then be sent through a DC blocking capacitor 607 followed by the known impedance 608 (e.g. a non-inductive resistor with only real impedance). In one example, the output waveform 613 can be approximately three-hundred (~300) mV in amplitude. The current can be set by the equation I=V/R; where V is controlled by the DAC and gain of the filtering/buffering amplifier 606. R can be the series combination of the fixed impedance 608, the source and sink electrode impedance, the tissue/electrode interface impedance and the tissue impedance 609.

The sink 614 for this current can be the DC voltage set by the high pass filter 607 that represents the virtual ground (e.g. the mid-rail voltage, or Vcc/2). This can also act as a bias for the tissue ensuring that the signal is centered within the operating range of the input amplifiers. Alternatively, DC blocking capacitors can be added to the inputs of the amplifier 610 as well as between the tissue 609 and ground 614 to allow the voltage of the tissue to float independent to the voltages found in the bioimpedance spectrometer system 101.

A set of electrodes can measure the induced voltage in the tissue as a result of the current and amplifies it with instrumentation amplifier 610. Another instrumentation amplifier 611 can measure and optionally amplifies the current passing through the known resistor. These amplifiers can be high-speed instrumentation amplifiers 601 capable of operating linearly up to a 1 MHz. These voltages can be scaled up or down by altering the gain of the amplifiers and/or by adjusting the voltage dividers that follow the amplifiers.

In one example, three (3) high-speed operation amplifiers 602-603 can be used in the place of the instrumentation amplifier 611 or 610. Two amplifiers 602 can be used as buffers to maintain high input impedance and the third amplifier 603 is used in a differential configuration. These amplifiers can be configured to provide any required gain and/or as unity gain. This configuration can enable a low power/low voltage operation while operating linearly (e.g. gain-wise) up to one (1) MHz. Additional filtering can be implemented before, after, or in conjunction with the amplifiers. This can include radio-frequency filtering and/or other type of filtering that counteracts environmental noise. For example, a high pass filter in the order of three-hundred (300) Hz can be used to block 50 Hz or 60 Hz line noise from being introduced into the circuit. Additionally, a radio-frequency interference (RFI) filter can be used to block RF interference from the wireless system.

The system must be designed such that the input voltages to the relative amplitude/phase detector IC are within the operating range of the IC. In the case of the AD8302, this range is from 223 uV to 223 mV. The gains provided by amplifiers 611 and 610 can be set to ensure that the signal falls within this operating range.

Other configurable parameters (for the AD8302, for example) include adjusting the mapping (e.g. slope) of output voltages 615 of the gain/phase detector 612 for a given input amplitude/phase difference. These parameters can be tuned to maximize sensitivity over the widest physiologically possible range present in the population. The output of the gain/phase detector 612 can then fed to the microcontroller 604 that digitizes the output using an analog digital converter (ADC). Analog or digital filtering can be applied to the output of the gain/phase detector 612. For example, several measurements can be made and averaged to reduce the output noise in the system. Also, the step size between different frequencies can be adjusted to produce more (and/or less) data points. Once the data has been collected, it can be sent upstream (e.g. via the telemetry system of FIG. 1 supra). Additionally, in some examples, computations can occur on the unit itself. The relative amplitude and phase data can be converted to real and imaginary impedance values. In the case of the AD8302 IC as the gain/phase measurement IC, this is accomplished by first converting the relative phase and gain output voltages 615 into a phase angle (α) and log ratio of amplitudes, as per the methodology described in the AD8302 datasheet (e.g. through linear or logarithmic mapping). The log ratio of amplitudes is then converted to a real impedance ($Z_r$). The geometric equation $$Z_i = \frac{\tan^{-1}(\alpha)}{Z_r}$$

can then be used to compute the imaginary impedance ($Z_i$) from the phase and real impedance.

Once the Real (Zr) and imaginary (Zi) components are known, they can be plotted on a cole-cole plot where the x-axis represents the real component and the y-axis represents the imaginary component of the complex impedance, over the range of frequencies. The curve can be extrapolated to intersect the x-axis at the points Zinf and Zo (extrapolated impedance at infinite frequency, and at DC). Zo can be proportional to the impedance of the extracellular fluid, and Zinf can be proportional to the impedance of all the fluid. In one example, the fluid status can be tracked as the ratio of the extracellular fluid to the total fluid. By tracking these variables (or a combination thereof), relative changes in edema can be computed. For example, with multiple days' worth of data acquired while the user is known to have normal fluid levels, a normal level for a user can be determined. Accordingly, any sudden changes to the level of extracellular fluid can be detected (e.g. by a measured increase in the ratio of extracellular fluid to total fluid).

Figure 7:
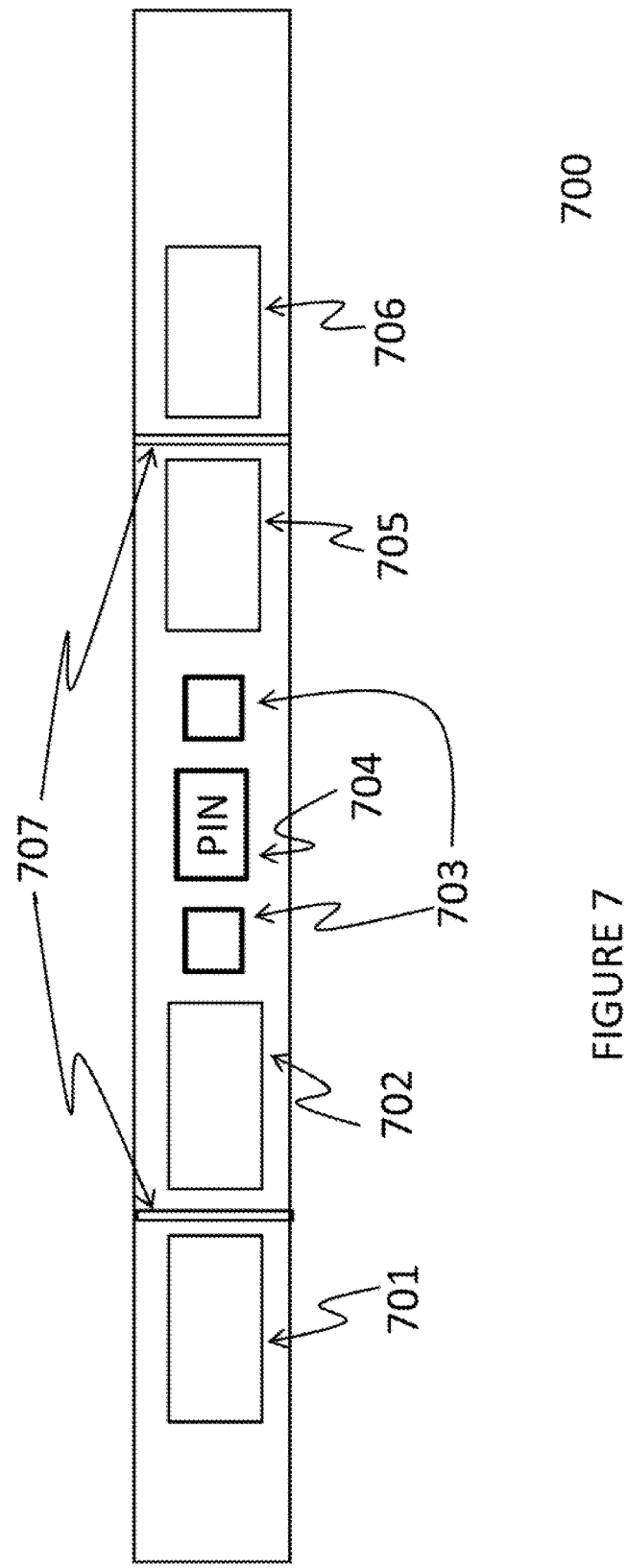
FIG. 7 depicts a strap that can incorporate the PPG and bioimpedance components to have optical contact to the skin, according to some examples.

FIG. 7 depicts a strap 700 that can incorporate the PPG components (e.g. LED 703 and/or photodiode 704 and/or optics) to have optical contact to the skin, according to some examples. The strap can be configured to isolate the LED(s) and the photodiode from each other (e.g. preventing light from the led to hit the photodiode without first traveling through the subject's tissue). The interface can be a light pipe and/or incorporate optics to help focus the light or increase the surface area of the photodiode. The LED and/or photodiode can be incorporated directly into the strap with either a small Printed circuit board (PCB, Flex PCB) including a portion of the amplification/filtering/conditioning circuit and/or tethered to the main circuit board with a ribbon cable or other connection mechanism (or the strap can expose holes for the led/photodiode which can reside on the main circuit board). The strap can also include a number of conductive surfaces for the bioimpedance circuit 701, 702, 705, 706. In one example, at least four (4) points are used which are insulated from each other. A strap can be composed of an array of conductive dry rubber electrodes. The strap can be used for the current source/sink and/or two pickup electrodes. Other strap examples can include conductive fabric electrodes (e.g. can be embedded into a garment as well as a "watch strap"), exposed metal electrodes, as well as any other type of electrode configuration. The measurement can be made while the wrist is motionless (e.g. as detected by the onboard accelerometer to help reduce motion related artifacts). These conductive surfaces can be rubber, silicon or metal embedded into the strap (or other conductive element). These pads can be spaced out or kept close together, as long as a sweat bridge cannot form between the conductive pads that could short out the pads. The strap can incorporate channels 707 which are raised/depressed relative to the pads to help prevent sweat bridge formation.

Figure 8:
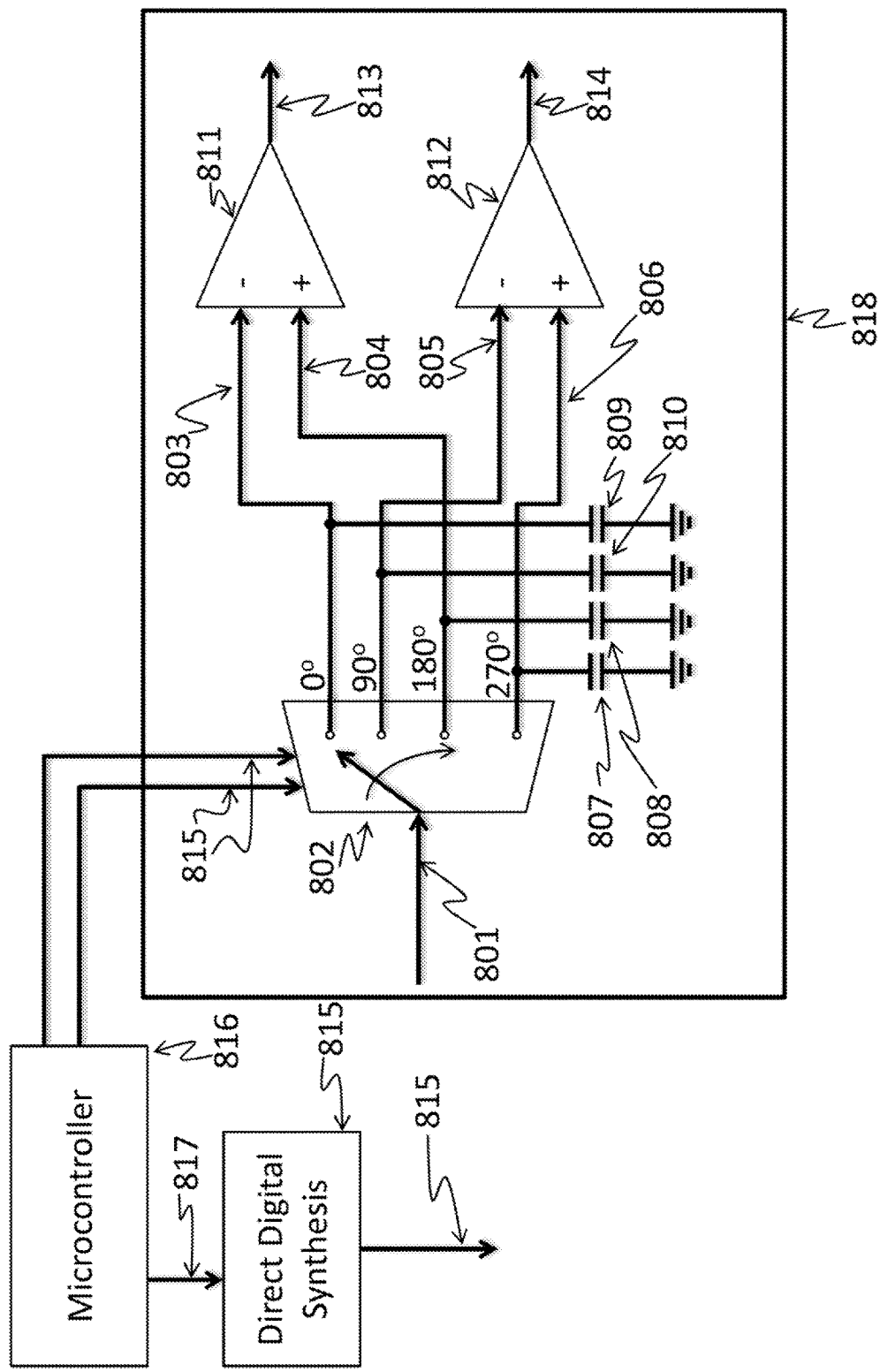
FIG. 8 is an example of an alternative method of measuring the complex impedance of a signal, according to some embodiments.

FIG. 8 is an example of an alternative method of measuring the complex impedance of a signal, according to some embodiments. System 818 is an IQ demodulator. The signal to be analyzed 801 is fed to a switch 802 (e.g. multiplexer, etc.) controlled by inputs 815 from a microcontroller, FPGA, CPLD, counter, etc. The switch will route the signal to four different outputs 803 804 805 806 depending on the phase of the signal. When the signal's phase is between 0-90 degrees, the switch will output the signal to 803. Likewise, at 90-180 degrees, 180-270 degrees, 270-360 degrees, etc., it will route the signal to 804 805 and 806, respectively. Thus the switch must cycle through the outputs at a rate of 4 times the input signal 801 frequency and be phase locked to the input frequency. The different signals 803 804 805 806 are then averaged on capacitors 807 808 810 809, respectively. Instrumentation amplifiers 811 will produce a voltage 813 proportional to the difference in voltages from capacitors 808 and 809 that represents the in-phase signal (I). Instrumentation amplifiers 812 will produce a voltage 814 proportional to the difference in voltages from capacitors 807 and 810 that represents the quadrature signal (Q). The signals 813 and 814 can then be converted to a numerical value using an analog to digital converter (not shown). The magnitude of the signal can be computed as the square root of the sum of the I squared and Q squared. The phase angle can be computed as the inverse tangent of the ratio Q to I.

Figure 9:
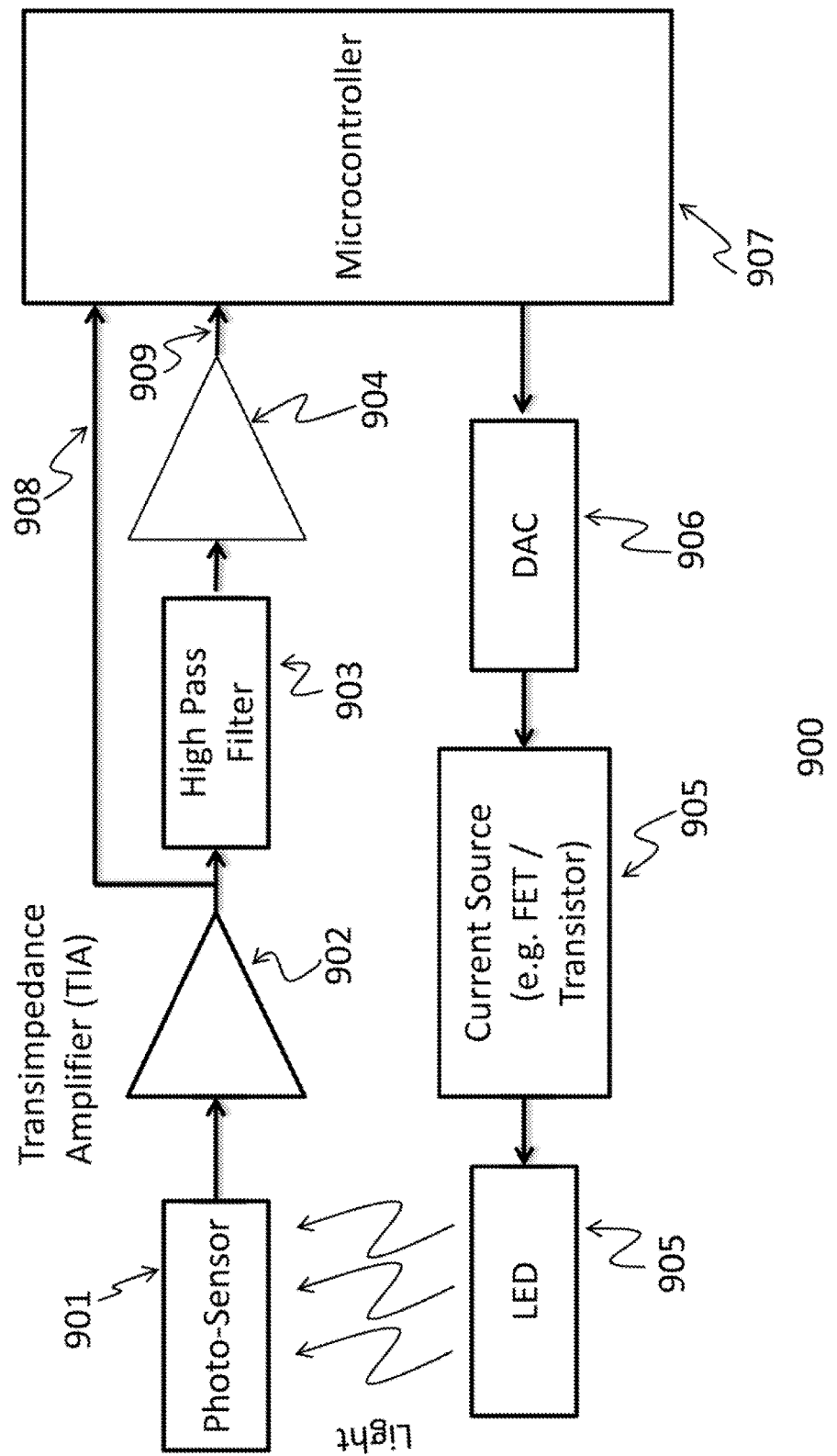
FIG. 9 illustrates an example of a system that can be used to implement a photoplethysmograph (PPG) system, according to some embodiments.

FIG. 9 illustrates an example of a system that can be used to implement a photoplethysmograph (PPG) system 900, according to some embodiments. A microcontroller (or other controlling device) can directly output a voltage through a built-in digital to analog converter (DAC) or an external DAC 906. The voltage can be converted to a current (e.g. using a transistor) 905 which is used to illuminate the LED(s) 910. The light passes through and/or is reflected 205 by the tissue to reach the photo-sensor 901. In one embodiment, the photo-sensor is a PIN Photodiode that is reversed biased to increase sensitivity and decrease capacitance. In one embodiment, the photodiode can generate a current proportional to incident light that is converted to a voltage through a transimpedance amplifier 902. The amplifier can be configured to low-pass filter frequencies that are physiologically relevant (e.g. DC-5 Hz) to reduce noise as well as to filter for any high frequency external light such as fluorescent lighting, or motion. To ensure that the input current from photosensor 901 (e.g. a photodiode) is within operating range of amplifier 902, the amplifier output 908 can be measured by the microcontroller (or other processing device) 907 and if it is too high or too low (e.g. out of the operating range of 902), the LED 910 current can adjusted by varying the output of the DAC 906. If the voltage 908 is too high (e.g. saturating) then the DAC 906 output can be reduced to reduce the LED current via transistor 905. If it is too low, then it can be increased via the same mechanism. When the voltage 908 is in the desired range, is can be high pass filtered 903 so as to keep the average signal voltage near the middle of the supply voltage range. An additional gain stage 904 can be implemented to further amplify the signal allowing for better beat detection. The output 909 can be sampled by the microcontroller 907 and either stored, transmitted, or processing applied to the signal. In some embodiments, filtration can occur using an active filter design in conjunction with amplifiers and/or various passive components (e.g. Independent of the amplifiers).

In some embodiments, PPG 900 photoplethysmograph system can utilize one LED frequency and the LED can remain illuminated throughout the duration of the measurement. This can allow for optimized analog filtering (e.g. a narrow bandwidth) of the signal of interest. When the LED is constantly on, then the transimpedance amplifier 902 bandwidth can be tuned to the exact bandwidth of the PPG signal (e.g. DC-5 Hz). This can significantly reduce the noise entering the system. For example, including just one LED frequency means that a photodiode can be selected which is maximally sensitive at the same frequency of the LED. This allows for lower LED current requirements, thus extending the battery life of the device. An infrared LED can be been chosen further reducing power consumption as photodiode sensitivities are typically greater for infrared light. Alternatively a green LED can be used due to its high level of absorption by the blood hemoglobin, and a corresponding photodiode that is maximally sensitive to the same green wavelength. The distance between the LED and photosensor/photodiode 901 can be increased forcing the light to travel through more tissue, increasing the SNR of the signal. Typically higher LED current is required to compensate for the greater LED/photodiode separation. In one example, the distance of six-point-three (6.3) mm provide a good compromise between power consumption and signal amplitude. Any number of LEDs can be used, according to various embodiments. A photodiode with a very large surface area can be used to further increase sensitivity. PPG system 900 is provided by way of example and not of limitation. Other PPG configurations can be utilized in other embodiments.

Figure 10:
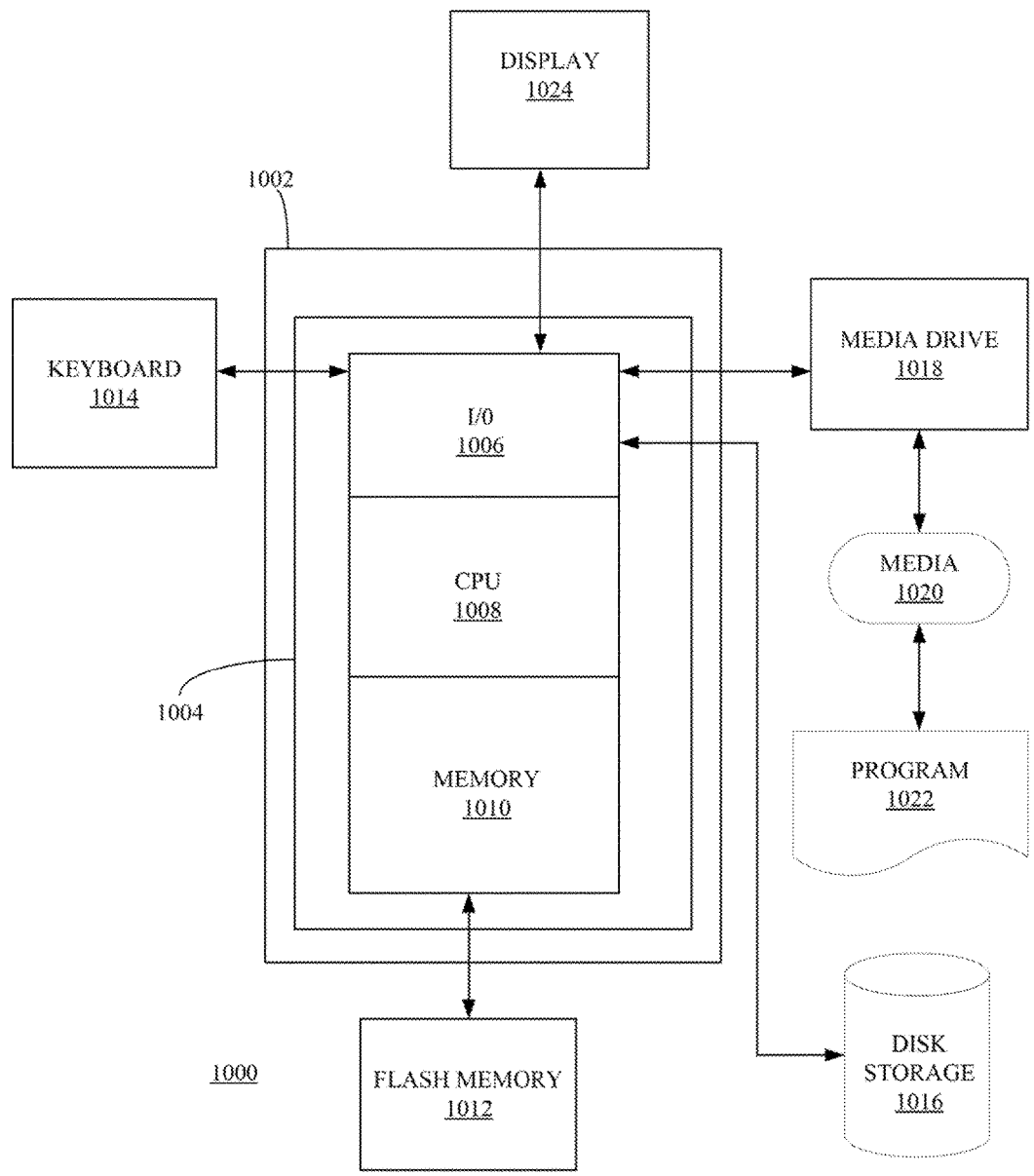
FIG. 10 depicts an exemplary computing system that can be configured to perform any one of the processes provided herein.

FIG. 10 depicts an exemplary computing system 1000 that can be configured to perform any one of the processes provided herein. In this context, computing system 1000 may include, for example, a processor, memory, storage, and I/O devices (e.g., monitor, keyboard, disk drive, Internet connection, etc.). However, computing system 1000 may include circuitry or other specialized hardware for carrying out some or all aspects of the processes. In some operational settings, computing system 1000 may be configured as a system that includes one or more units, each of which is configured to carry out some aspects of the processes either in software, hardware, or some combination thereof.

FIG. 10 depicts computing system 1000 with a number of components that may be used to perform any of the processes described herein. The main system 1002 includes a motherboard 1004 having an I/O section 1006, one or more central processing units (CPU) 1008, and a memory section 1010, which may have a flash memory card 1012 related to it. The I/O section 1006 can be connected to a display 1014, a keyboard and/or other user input (not shown), a disk storage unit 1016, and a media drive unit 1018. The media drive unit 1018 can read/write a computer-readable medium 1020, which can contain programs 1022 and/or data. Computing system 1000 can include a web browser. Moreover, it is noted that computing system 1000 can be configured to include additional systems in order to fulfill various functionalities. Computing system 1000 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

In some embodiments, the low-impedance or high-impedance current source circuit can maintain a specified-range of a 100 uA-100 mA value of the AC current passing through the user's tissue. The bioimpedance spectrometer can propagate the AC current at frequencies from 1 kHz to 1 Mhz). The processing module can measure the magnitude of impedance at a 1 Khz frequency and a high 1 Mhz frequency. The processing module can compare a magnitude of the impedance of the tissue at both low (e.g. 1 kHz) and high (e.g. 1 Mhz) frequencies and based on these impedance values determines the amount of intracellular and extracellular fluid from the complex impedance value. The third voltage signal is band-pass filtered to zero point three (0.3 Hz) to five (5) Hertz (Hz) to reduce the noise and external interference of the third voltage signal.

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it can be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

What is claimed as new and desired to be protected by Letters Patent of the United States is:

1. A bioimpedance spectrometer system comprising:
   a strap configured to be worn on a user's body;
   a bioimpedance circuit on the strap, the bioimpedance circuit comprising:
      two current-delivery electrodes configured to convey an alternating current (AC) signal through a user's tissue;
      a high-impedance current source circuit that maintains the AC signal within a specified-range;
      two sense electrodes configured to detect a differential voltage on the user's tissue;
      an amplifier that is configured to measure the differential voltage on the user's tissue between the two sense electrodes, wherein the amplifier is a low power/low voltage amplifier configured to measure a differential voltage across a known resistor that is in series with the two current-delivery electrodes, further wherein the low power/low voltage amplifier comprises a combination of operational amplifiers configured to provide a differential voltage output at a low power and low voltage while operating linearly up to one MHz;
      a gain/phase measurement circuit connected to both the amplifier that is configured to measure the differential voltage on the user's tissue and the low power/low voltage amplifier, wherein the gain/phase measurement circuit is configured to determine an amplitude and phase difference between the differential voltage between the two sense electrodes on the user's tissue and the differential voltage across the known resistor; and a processing module configured to receive input from the gain/phase measurement circuit and to calculate an impedance magnitude or a complex impedance value from the amplitude and phase difference and to determine a relative amount of intracellular and extracellular fluid from the impedance magnitude or complex impedance value.

2. The bioimpedance spectrometer system of claim 1, wherein the two current-delivery electrodes and the two sense electrodes are in a tetrapolar configuration.

3. The bioimpedance spectrometer system of claim 1, wherein the amplifier that measures the differential voltage on the user's tissue between the two sense electrodes comprises a combination of operational amplifiers configured to provide a differential voltage output.

4. The bioimpedance spectrometer system of claim 1, wherein a frequency of the AC current is set to specified frequencies between 1 KHz and 1 MHz.

5. The bioimpedance spectrometer system of claim 4, wherein the impedance magnitude or complex impedance is calculated at one or more specified frequencies.

6. The bioimpedance spectrometer system of claim 1, wherein the processing module fits the calculated impedance magnitude or complex impedance to a Cole-Cole plot and extrapolates the real impedance at a direct current (DC) and at an infinite frequency.

7. The bioimpedance spectrometer system of claim 6, wherein the processing module calculates the impedance magnitude at a low frequency and a high frequency.

8. The bioimpedance spectrometer system of claim 7, wherein the processing module is configured to determine the relative amount of intracellular and extracellular fluid by comparing the impedance magnitude or complex at both a low and a high frequencies.

9. The bioimpedance spectrometer system of claim 1, wherein the amplifier that is configured to measure the differential voltage on the user's tissue and the low power/low voltage amplifier are configured to provide input voltages to the amplitude/phase measurement circuit that are between 223 µV to 223 mV.

10. The bioimpedance spectrometer system of claim 1, wherein the high-impedance current source circuit maintains the AC signal within a specified-range of between 100 µA to 100 mA.

11. The bioimpedance spectrometer system of claim 1, wherein the processing module comprises a microcontroller.

12. The bioimpedance spectrometer system of claim 1, wherein the strap is configured to be worn on the user's wrist.

13. A bioimpedance spectrometer system comprising:
a strap configured to be worn on a user's wrist;
a bioimpedance circuit on the strap, the bioimpedance circuit comprising:
two current-delivery electrodes configured to convey an alternating current (AC) signal through a user's wrist;
a high-impedance current source circuit that maintains the AC signal within a specified-range;
two sense electrodes configured to detect a differential voltage on the user's wrist;
an amplifier that is configured to measure the differential voltage on the user's wrist between the two sense electrodes wherein the amplifier is a low power/low voltage amplifier configured to measure a differential voltage across a known resistor that is in series with the two current electrodes, further wherein the low power/low voltage amplifier comprises two high-speed operational amplifiers configured as buffers to maintain high input impedance and a third operational amplifier in a differential configuration such that the low power/low voltage amplifier operates linearly up to one MHz;
a gain/phase measurement circuit connected to the amplifier configured to measure the differential voltage on the user's wrist and the low power/low voltage amplifier and configured to determine an amplitude and phase difference between the differential voltage between two sense electrodes and the differential voltage across the known resistor; and
a microprocessor configured to calculate an impedance magnitude or a complex impedance value from the amplitude and phase difference and determines a relative amount of intracellular and extracellular fluid from the impedance magnitude or complex impedance value.

14. A bioimpedance spectrometer system comprising:
a strap configured to be worn on a user's appendage; and
a bioimpedance circuit on the strap, the bioimpedance circuit comprising:
two current-delivery electrodes configured to convey an alternating current (AC) signal through a user's appendage;
a high-impedance current source circuit that maintains the AC signal within a specified-range;
two sense electrodes configured to detect a differential voltage on the user's appendage;
an amplifier configured to measure the differential voltage on the user's appendage between the two sense electrodes wherein the amplifier is a low power/low voltage amplifier configured to measure a differential voltage across a known resistor that is in series with the two current electrodes, further wherein the low power/low voltage amplifier comprises a combination of operational amplifiers configured to provide a differential voltage output at a low power and low voltage while operating linearly up to one MHz;
a gain/phase measurement circuit connected to the amplifier configured to measure the differential voltage on the user's appendage and the low power/low voltage amplifier and configured to determine a ratio of the differential voltage between two sense electrodes and the differential voltage across the known resistor; and
a microprocessor configured to calculate an impedance magnitude or a complex impedance value from the ratio of the differential voltage across the known resistor and the differential voltage across the known resistor, and determines a relative amount of intracellular and extracellular fluid from the impedance magnitude or complex impedance value.

* * * * *

UNITED STATES PATENT AND TRADEMARK OFFICE
CERTIFICATE OF CORRECTION

| | | |
|---|---|---|
| PATENT NO. | : 10,004,408 B2 | Page 1 of 1 |
| APPLICATION NO. | : 14/958915 | |
| DATED | : June 26, 2018 | |
| INVENTOR(S) | : Reza Naima | |

It is certified that error appears in the above-identified patent and that said Letters Patent is hereby corrected as shown below:

In the Specification

Column 1, Line 13, please add the following:
REFERENCE TO GOVERNMENT
This invention was made with Government support under Grant No. 2R44HL125001-02 and 5R44HL125001-03 awarded by the National Institutes of Health. The Government has certain rights in this invention.

Signed and Sealed this
Eleventh Day of August, 2020

Andrei Iancu
*Director of the United States Patent and Trademark Office*